(12) United States Patent
Tsuyuki

(10) Patent No.: US 11,404,159 B2
(45) Date of Patent: Aug. 2, 2022

(54) MEDICAL INFORMATION PROCESSING SYSTEM AND MEDICAL INFORMATION PROCESSING APPARATUS

(71) Applicant: CANON MEDICAL SYSTEMS CORPORATION, Otawara (JP)

(72) Inventor: Masaharu Tsuyuki, Nasushiobara (JP)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 148 days.

(21) Appl. No.: 16/846,703

(22) Filed: Apr. 13, 2020

(65) Prior Publication Data

US 2020/0335203 A1     Oct. 22, 2020

(30) Foreign Application Priority Data

Apr. 16, 2019 (JP) .............................. JP2019-077701

(51) Int. Cl.
*G06K 9/00* (2022.01)
*G16H 30/40* (2018.01)
*G16H 30/20* (2018.01)
*G06T 3/40* (2006.01)
*G06N 3/08* (2006.01)
(Continued)

(52) U.S. Cl.
CPC ............... *G16H 30/40* (2018.01); *G06N 3/04* (2013.01); *G06N 3/08* (2013.01); *G06T 3/40* (2013.01); *G16H 30/20* (2018.01); *G16H 50/20* (2018.01)

(58) Field of Classification Search
CPC .. A61K 38/4893; A61K 47/02; A61K 9/0019; A61K 38/48; A61B 6/032; A61B 6/52; A61B 6/5211; A61B 6/563; A61B 8/5215; A61B 8/565; A61P 21/00; A61P 21/02; A61P 25/14; A61P 25/28; C12Y 304/24069; G06F 19/321; G06T 2207/10116; G06T 2207/30061; G06T 5/009; G06T 7/0012; G06T 9/004; G06T 9/005; H04N 19/115; H04N 19/14; H04N 19/172; H04N 19/197; H04N 19/593; H04N 19/63; H04N 19/91; H04N 19/154; H04N 19/162; Y02A 50/30; Y02A 50/469; B60J 1/2047; B60J 1/2063; B60R 21/231; B60R 21/235; G16H 30/20; G16H 30/40;
(Continued)

(56) References Cited

U.S. PATENT DOCUMENTS 6,608,915 B2  8/2003  Tsujii
9,111,345 B2  8/2015  Sato et al.
(Continued)

*Primary Examiner* — Xin Jia
(74) *Attorney, Agent, or Firm* — Oblon, McClelland, Maier & Neustadt, L.L.P.

(57) ABSTRACT

A first processor of embodiments outputs intermediate data with a quantity less than that of third medical image data by inputting the third medical image data to a compression model including an input layer and a middle layer from two trained models obtained by dividing, on the basis of the middle layer, a trained model which has been trained such that second medical image data is output from an output layer by inputting first medical image data to the input layer. A second processor outputs fourth medical image data with a quantity greater than that of the intermediate data by inputting the intermediate data acquired from the first processor via a network to an expansion model including the output layer from the two trained models.

11 Claims, 10 Drawing Sheets

(51) Int. Cl.
*G06N 3/04* (2006.01)
*G16H 50/20* (2018.01)

(58) Field of Classification Search
CPC ................ Y10S 148/085; Y10T 29/42; Y10T 428/1328; Y10T 428/1352; Y10T 428/219
See application file for complete search history.

(56) References Cited

U.S. PATENT DOCUMENTS

| | | |
|---|---|---|
| 2015/0172681 A1 | 6/2015 | Kim et al. |
| 2019/0042870 A1* | 2/2019 | Chen ........................ H04L 67/12 |
| 2019/0122075 A1* | 4/2019 | Zhang ..................... G06N 20/20 |

\* cited by examiner

57

91

MEDICAL INFORMATION PROCESSING SYSTEM AND MEDICAL INFORMATION PROCESSING APPARATUS

CROSS-REFERENCE TO RELATED APPLICATION

Priority is claimed on Japanese Patent Application No. 2019-077701, filed Apr. 16, 2019, the content of which is incorporated herein by reference.

FIELD

Embodiments disclosed in the present description and drawings relate to a medical information processing system and a medical information processing apparatus.

BACKGROUND

There are cases in which medical image data generated by diagnostic apparatuses such as an X-ray computed tomography (CT) apparatus, a magnetic resonance (MR) apparatus, and the like is compressed and stored in a server and the like. Various types of literature in which a level of a compression ratio at which medical image data is compressed is studied are known. However, since details of compression processing focusing on suitable adjustment of the definition of an image obtained by expanding a compressed image are not set in conventional technology, there are cases in which compression is insufficient or the definition of the expanded image deteriorates.

DETAILED DESCRIPTION

An object of embodiments disclosed in the present description and drawings is to reduce resource consumption while maintaining a desired level of definition after expansion.

A medical information processing system of embodiments includes a first processor and a second processor. The first processor outputs intermediate data with a quantity less than that of third medical image data by inputting the third medical image data to a compression model including an input layer and a middle layer from two trained models obtained by dividing, on the basis of the middle layer, a trained model which includes the input layer having a first number of nodes, an output layer having a second number of nodes, and the middle layer that is interposed between the input layer and the output layer and has a number of nodes less than the first number of nodes and the second number of nodes, and has been trained such that second medical image data is output from the output layer by inputting first medical image data to the input layer. The second processor outputs fourth medical image data with a quantity greater than that of the intermediate data by inputting the intermediate data acquired from the first processor via a network to an expansion model including the output layer from the two trained models.

Hereinafter, a medical information processing system and a medical information processing apparatus of embodiments will be described with reference to the drawings. The medical information processing system is realized by one or more processors. The medical information processing system includes a first processor and a second processor. The first processor and the second processor may be realized by separate devices or a single device. Medical image data in the following description may be two-dimensional data (plane data) or three-dimensional data (volume data).

Figure 1:
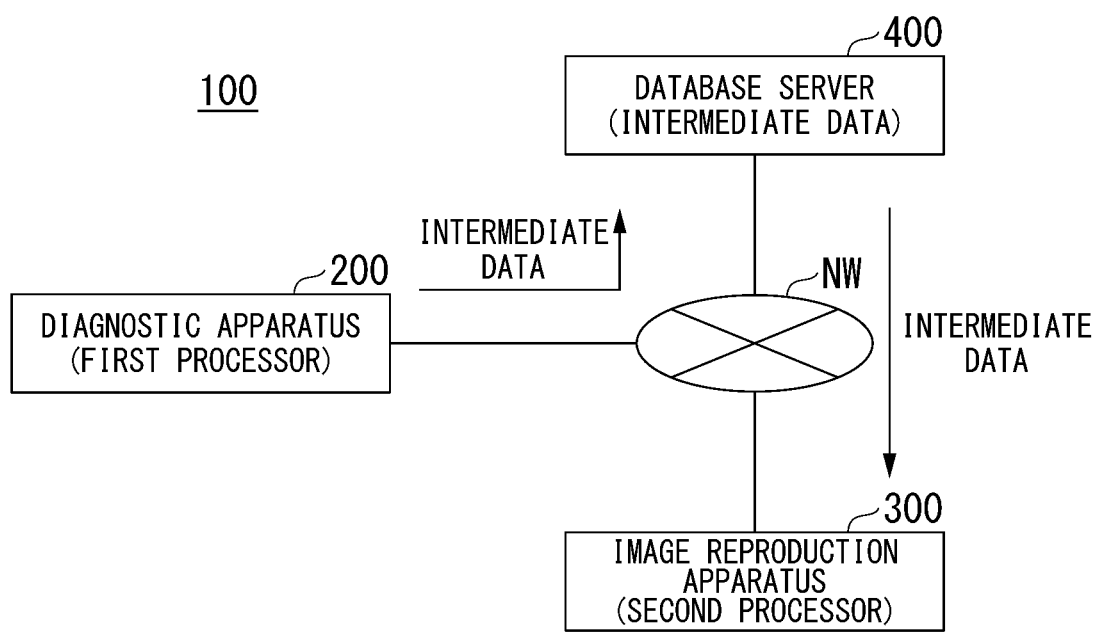
FIG. 1 is a diagram showing an example of a configuration of a medical information processing system.

FIG. 1 is a diagram showing an example of a configuration of a medical information processing system 100. The medical information processing system 100 is realized, for example, by a diagnostic apparatus 200 including a first processor and an image reproduction apparatus 300 including a second processor. In this example, each of the diagnostic apparatus 200 and the image reproduction apparatus 300 is an example of a medical information processing apparatus. The diagnostic apparatus 200 is an example of the first processing circuitry, the image reproduction apparatus 300 is an example of the second processing circuitry.

The diagnostic apparatus 200 is any apparatus capable of generating medical image data, such as an X-ray CT apparatus, an MR apparatus, a PET apparatus, a SPECT apparatus, an ultrasonic diagnostic apparatus, and a nuclear medical diagnostic apparatus. The first processor of the diagnostic apparatus 200 inputs generated medical image data (third medical image data) to a compression model to output intermediate data with a quantity less than that of the medical image data. The diagnostic apparatus 200 transmits the intermediate data to a database server 400 via a network NW and causes the database server 400 to store the intermediate data. The network NW includes, for example, a wide area network (WAN), a local area network (LAN), the Internet, and the like.

The image reproduction apparatus 300 is an apparatus by which medial images based on medical image data generated by the diagnostic apparatus 200 can be viewed. The image reproduction apparatus 300 and the diagnostic apparatus 200 may be installed in the same facility (for example, a hospital) or installed in different facilities. In addition, the image reproduction apparatus 300 may be an apparatus included in the diagnostic apparatus 200. The image reproduction apparatus 300 acquires intermediate data from the database server 400 via the network NW and inputs the intermediate data to an expansion model to output medical image data (fourth medical image data) for viewing which has a quantity greater than that of the intermediate data and to cause a display device to display the medical image data for viewing.

The compression model includes an input layer and a middle layer from two trained models obtained by dividing a trained model on the basis of the middle layer. The expansion model includes an output layer from the two trained models obtained by dividing a trained model on the basis of the middle layer. The trained model is not divided into the compression model and the expansion model and trained but is integrally trained as a model before division. Accordingly, the medical information processing system 100 can perform compression processing to an appropriate degree while maintaining definition after expansion.

An arrangement of the first processor and the second processor shown in FIG. 1 is merely an example and the first processor and the second processor can be arranged at any positions. For example, the first processor may be realized by an apparatus separate from the diagnostic apparatus and the database server 400 may have functions of the first processor and/or the second processor.

An example of a specific form will be described below on the assumption that the diagnostic apparatus 200 is an X-ray CT apparatus and the image reproduction apparatus 300 is a terminal apparatus installed in the same facility as that where the X-ray CT apparatus is installed.

First Embodiment

[X-Ray CT Apparatus]

Figure 2:
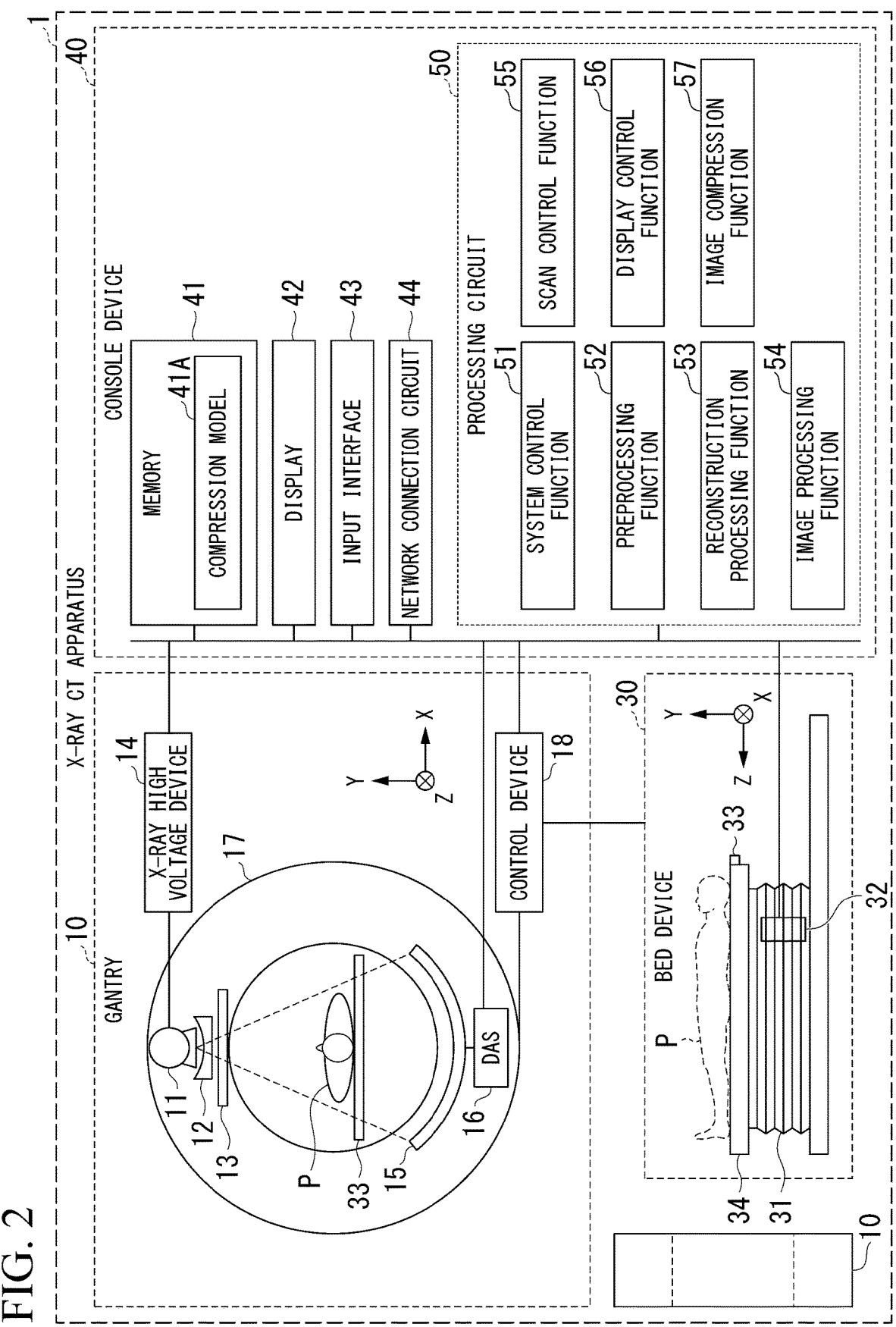
FIG. 2 is a configuration diagram of an X-ray CT apparatus corresponding to a diagnostic apparatus.

FIG. 2 is a configuration diagram of an X-ray CT apparatus 1 corresponding to the diagnostic apparatus 200. The X-ray CT apparatus 1 includes, for example, a gantry 10, a bed device 30, and a console device 40. Although FIG. 2 shows both a diagram of the gantry 10 viewed in a Z-axis direction and a diagram viewed in an X-axis direction for convenience of description, there is actually one gantry 10. In embodiments, a rotation axis of a rotary frame 17 in a non-tilted state or a longitudinal direction of a top board 33 of the bed device 30 is defined as a Z-axis direction, an axis at a right angle to the Z-axis direction that is parallel to the floor is defined as an X-axis direction, and a direction at a right angle to the Z-axis direction that is perpendicular to the floor is defined as a Y-axis direction.

The gantry 10 includes, for example, an X-ray tube 11, a wedge 12, a collimator 13, an X-ray high voltage device 14, an X-ray detector 15, a data collection system (hereinafter, data acquisition system (DAS)) 16, the rotary frame 17 and a control device 18.

The X-ray tube 11 generates X rays by radiating thermions from a cathode (filament) to an anode (target) according to application of a high voltage from the X-ray high voltage device 14. The X-ray tube 11 includes a vacuum tube. For example, the X-ray tube 11 may be a rotating anode type X-ray tube which generates X rays by radiating thermions to a rotating anode.

The wedge 12 is a filter for controlling the amount of X rays radiated from the X-ray tube 11 to an examination subject P. The wedge 12 attenuates X rays transmitted through the wedge 12 such that a distribution of the amount of X rays radiated from the X-ray tube 11 to the examination subject P becomes a predetermined distribution. The wedge 12 is also called a wedge filter or a bow-tie filter. For example, the wedge 12 may be manufactured by processing aluminum such that it has a predetermined target angle and a predetermined thickness.

The collimator 13 is a mechanism for narrowing a radiation range of X rays that have been transmitted through the wedge 12. The collimator 13 narrows a radiation range of X rays, for example, by forming a slit according to combination of a plurality of lead plates. The collimator 13 may also be called an X-ray aperture. A narrowing range of the collimator 13 may be mechanically driven.

The X-ray high voltage device 14 includes, for example, a high voltage generation device and an X-ray control device. The high voltage generation device has an electric circuit including a transformer (trans), a rectifier, and the like and generates a high voltage to be applied to the X-ray tube 11. The X-ray control device controls an output voltage of the high voltage generation device in response to the amount of X rays generated by the X-ray tube 11. The high voltage generation device may perform voltage boosting through the aforementioned transformer or perform voltage boosting through an inverter. The X-ray high voltage device 14 may be provided in the rotary frame 17 or provided on the side of a fixed frame (not shown) of the gantry 10.

The X-ray detector 15 detects the intensity of X rays that have been generated by the X-ray tube 11, passed through the examination subject P and applied to the X-ray detector 15. The X-ray detector 15 outputs an electrical signal (an optical signal or the like is also possible) in response to the detected intensity of X rays to the DAS 18. The X-ray detector 15 includes, for example, a plurality of X-ray detection element strings. The plurality of X-ray detection element strings are obtained by arranging a plurality of X-ray detection elements in a channel direction along an arc having the focus of the X-ray tube 11 as a center. The plurality of X-ray detection element strings are arranged in a slice direction (row direction).

The X-ray detector 15 is, for example, an indirect detector including a grid, a scintillator array and an optical sensor array. The scintillator array includes a plurality of scintillators. Each scintillator has scintillator crystals. Scintillator crystals emit an amount of light in response to the intensity of input X rays. The grid is disposed on a surface of the scintillator array to which X rays are input and includes an X-ray shielding plate having a function of absorbing scattered X rays. Meanwhile, there is a case in which the grid is called a collimator (one-dimensional collimator or two-dimensional collimator). The optical sensor array includes, for example, optical sensors such as photomultipliers (PMTs). The optical sensor array outputs an electrical signal in response to the amount of light emitted from the scintillators. The X-ray detector 15 may be a direct conversion type detector including a semiconductor element which converts input X rays into an electrical signal.

The DAS 16 includes, for example, an amplifier, an integrator, and an A/D converter. The amplifier performs amplification processing on an electrical signal output from each X-ray detection element of the X-ray detector 15. The integrator integrates amplified electrical signals over a view period (which will be described later). The A/D converter converts an electrical signal representing an integration result into a digital signal. The DAS 16 outputs detection data based on the digital signal to the console device 40. The detection data is a digital value of an X-ray intensity identified through a channel number and a string number of an X-ray detection element that is a generation source, and a view number indicating a collected view. A view number is a number that varies according to rotation of the rotary frame 17 and is, for example, a number that increases according to rotation of the rotary frame 17. Accordingly, a view number is information representing a rotation angle of the X-ray tube 11. A view period is a period from a rotation angle corresponding to a certain view number to a rotation angle corresponding to the next view number. The DAS 16 may detect view switching through a timing signal input from the control device 18, an internal timer, or a signal acquired from a sensor which is not shown. When X rays are continuously emitted by the X-ray tube 11 during full scanning, the DAS 16 collects detection data groups corresponding to the entire circumference (360 degrees). When X rays are continuously emitted by the X-ray tube 11 during half scanning, the DAS 16 collects detection data corresponding to half a circumference (180 degrees).

The rotary frame 17 is an annular member which supports the X-ray tube 11, the wedge 12, the collimator 13 and the X-ray detector 15 such that the X-ray tube 11, the wedge 12 and the collimator 13 face the X-ray detector 15. The rotary frame 17 is rotatably supported by a fixed frame having the examination subject P introduced thereinto as a center. The rotary frame 17 additionally supports the DAS 16. Detection data output from the DAS 16 is transmitted from a transmitter having a light emitting diode (LED) provided in the rotary frame 17 to a receiver having a photodiode provided in a non-rotary part (e.g., a fixed frame) of the gantry 10 through optical communication and forwarded to the console device 40 through the receiver. Meanwhile, a method of transmitting detection data from the rotary frame 17 to a non-rotary part is not limited to the aforementioned method using optical communication and any non-contact type transmission method may be employed. The rotary frame 17 is not limited to an annular member and may be a member such as an arm as long as it can support and rotate the X-ray tube 11 and the like.

Although the X-ray CT apparatus 1 may be, for example, a Rotate/Rotate-Type X-ray CT apparatus (third-generation CT) in which both the X-ray tube 11 and the X-ray detector 15 are supported by the rotary frame 17 and rotate around the examination subject P, it is not limited thereto and may be a Stationary/Rotate-Type X-ray CT apparatus (fourth-generation CT) in which a plurality of X-ray detection elements arranged in an annular shape are fixed to a fixed frame and the X-ray tube 11 rotates around the examination subject P.

The control device 18 includes, for example, a processing circuit having a processor such as a central processing unit (CPU) and a driving mechanism including a motor, an actuator and the like. The control device 18 receives an input signal from an input interface 43 attached to the console device 40 or the gantry 10 and controls operations of the gantry 10 and the bed device 30. For example, the control device 18 may rotate the rotary frame 17, tilt the gantry 10 or move the top board 33 of the bed device 30. When the control device 18 tilts the gantry 10, the control device 18 rotates the rotary frame 17 on an axis parallel to the Z-axis direction on the basis of an inclination angle (tilt angle) input to the input interface 43. The control device 18 ascertains a rotation angle of the rotary frame 17 through an output of a sensor which is not shown, and the like. In addition, the control device 18 provides the rotation angle of the rotary frame 17 to a scan control function 55 at any time. The control device 18 may be provided in the gantry 10 or provided in the console device 40.

The bed device 30 moves the examination subject P to be scanned mounted thereon and introduces the examination subject P into the rotary frame 17 of the gantry 10. The bed device 30 includes, for example, a base 31, a bed driving device 32, the top board 33, and a supporting frame 34. The base 31 includes a housing which supports the supporting frame 34 such that the supporting frame 34 can move in a vertical direction (Y-axis direction). The bed driving device 32 includes a motor and an actuator. The bed driving device 32 moves the top board 33 on which the examination subject P is mounted in the longitudinal direction (Z-axis direction) of the top board 33 along the supporting frame 34. The top board 33 is a plate-shaped member on which the examination subject P is mounted.

The bed driving device 32 may move the supporting frame 34 in the longitudinal direction of the top board 33 as well as the top board 33. Further, contrary to the above, the gantry 10 may be movable in the Z-axis direction and the rotary frame 17 may be controlled such that it comes near the examination subject P in accordance with movement of the gantry 10. In addition, both the gantry 10 and the top board 33 may be configured such that they are movable. Furthermore, the X-ray CT apparatus 1 may be a type of apparatus in which the examination subject P is scanned in a lying position or a sitting position. In this case, the X-ray CT apparatus 1 has an examination subject supporting function instead of the bed device 30 and the gantry 10 rotates the rotary frame 17 in an axial direction perpendicular to the floor.

The console device 40 includes, for example, a memory 41, a display 42, the input interface 43, and a processing circuit 50. Although the console device 40 is described as a body separate from the gantry 10 in embodiments, some or all components of the console device 40 may be included in the gantry 10.

The memory 41 is realized, for example, by a semiconductor element such as a random access memory (RAM) or a flash memory, a hard disk, an optical disc, or the like. The memory 41 stores, for example, detection data, projection data, reconstructed image data, CT image data, a compression model 41A, and the like. Such data may be stored in an external memory with which the X-ray CT apparatus 1 can communicate instead of the memory 41 (or in addition to the memory 41). For example, the external memory may be controlled through a cloud server which manages the external memory by receiving a read request.

The display 42 displays various types of information. For example, the display 42 displays medical images (CT images) generated by a processing circuit, graphical user interface (GUI) images through which various operations from an operator are received, and the like. For example, the display 42 may be a liquid crystal display, a cathode ray tube (CRT), an organic electroluminescence (EL) display, or the like. The display 42 may be provided in the gantry 10. The display 42 may be a desktop type or a display device (e.g., a tablet terminal) which can wirelessly communicate with the main body of the console device 40.

The input interface 43 receives various input operations from an operator and outputs electrical signals representing details of received input operations to the processing circuit 50. For example, the input interface 43 may receive operations of inputting collection conditions when detection data or projection data (which will be described later) is collected, reconstruction conditions when a CT image is reconstructed, image processing conditions when a postprocessing image is generated from a CT image, and the like. For example, the input interface 43 may be realized by a mouse, a keyboard, a touch panel, a trackball, a switch, a button, a joystick, a camera, an infrared sensor, a microphone, or the like. The input interface 43 may be provided in the gantry 10. In addition, the input interface 43 may be realized by a display device (e.g., a tablet terminal) which can wirelessly communicate with the main body of the console device 40.

A network connection circuit 44 includes, for example, a network card having a printed circuit board, a wireless communication module, or the like. The network connection circuit 44 implements an information communication protocol in accordance with the form of a network to be connected thereto.

The processing circuit 50 controls the overall operation of the X-ray CT apparatus 1. The processing circuit 50 is an example of the first processor. The processing circuit 50 executes, for example, a system control function 51, a preprocessing function 52, a reconstruction processing function 53, an image processing function 54, the scan control function 55, a display control function 56, and the like. For example, these functions may be realized by a hardware processor executing a program (software) stored in the memory 41. The hardware processor refers to, for example, a circuit (circuitry) such as a central processing unit (CPU), a graphics processing unit (GPU), an application specific integrated circuit (ASIC), a field-programmable gate array (FPGA), or a graphics processing unit (GPU), a programmable logic device (e.g., a simple programmable logic device (SPLD)), a complex programmable logic device (CPLD), or a field programmable gate array (FPGA). The program may be directly incorporated into the circuit of the hardware processor instead of being stored in the memory 41. In this case, the hardware processor realizes functions by reading and executing the program incorporated into the circuit. The hardware processor is not limited to a configuration as a single circuit and may be configured as a single hardware processor by combining a plurality of independent circuits to realize respective functions. Furthermore, a plurality of components may be integrated into a single hardware processor to realize respective functions.

Components included in the console device 40 or the processing circuit 50 may be distributed and realized by a plurality of hardware circuits. The processing circuit 50 may be realized by a processing device which can communicate with the console device 40 instead of being included in the console device 40. For example, the processing device may be a workstation connected to a single X-ray CT apparatus or a device (e.g., a cloud server) which is connected to a plurality of X-ray CT apparatuses and integrally executes processes equivalent to those of the processing circuit 50 which will be described below.

The system control function 51 controls various functions of the processing circuit 50 on the basis of input operations received through the input interface 43.

The preprocessing function 52 performs preprocessing such as logarithmic conversion processing, offset correction processing, inter-channel sensitivity correction processing and beam hardening correction on detection data output from the DAS 16 and generates projection data.

The reconstruction processing function 53 performs reconstruction processing using a filter correction reverse projection method, a sequential approximation reconstruction method or the like on projection data generated by the preprocessing function 52 to generate CT image data and stores the generated CT image data in the memory 41.

The image processing function 54 converts CT image data into three-dimensional image data or section image data with an arbitrary section through a known method on the basis of an input operation received by the input interface 43. Conversion into three-dimensional image data may be performed by the preprocessing function 52.

The scan control function 55 instructs the X-ray high voltage device 14, the DAS 16, the control device 18 and the bed driving device 32 to control detection data collection processing in the gantry 10. The scan control function 55 controls operation of each component when imaging for collecting positioning images and capturing of images used for diagnosis are performed.

The display control function 56 causes the display 42 to display various images.

According to the above-described configuration, the X-ray CT apparatus 1 scans the examination subject P in a scan mode such as helical scan, conventional scan or step-and-shot. The helical scan is a mode of rotating the rotary frame 17 while moving the top board 33 to scan the examination subject P in a spiral form. The conventional scan is a mode of rotating the rotary frame 17 in a state in which the top board 33 is stopped to scan the examination subject P in a circular orbit. The step-and-shot is a mode of moving the position of the top board 33 at specific intervals to perform the conventional scan in a plurality of scan areas.

An image compression function 57 compresses various images and generates intermediate data using the compression model 41A stored in the memory 41. The image compression function 57 transmits the generated intermediate data to the database server 400 via the network NW using the network connection circuit 44. Processing of generating the intermediate data will be described in detail later.

[Terminal Apparatus]

Figure 3:
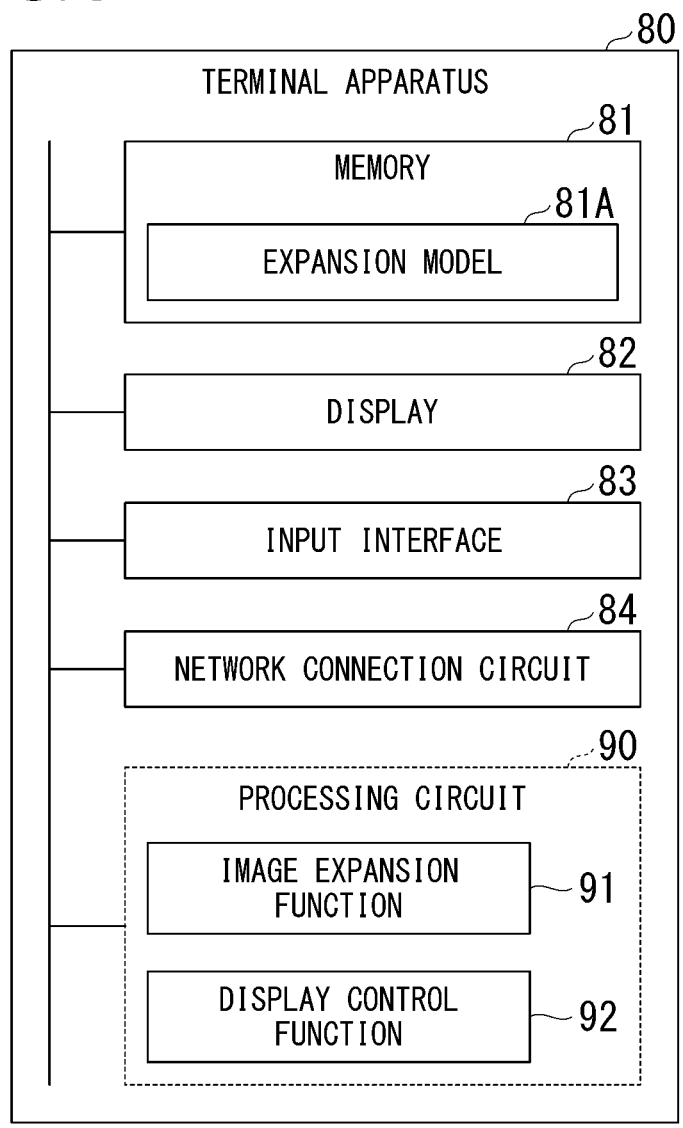
FIG. 3 is a configuration diagram of a terminal apparatus corresponding to an image reproduction apparatus.

FIG. 3 is a configuration diagram of a terminal apparatus 80 corresponding to the image reproduction apparatus 300. The terminal apparatus 80 includes, for example, a memory 81, a display 82, an input interface 83, a network connection circuit 84, and a processing circuit 90.

The memory 81 is realized by, for example, a semiconductor memory element such as a RAM or a flash memory, a hard disk, an optical disc, or the like. The memory 81 stores, for example, an expansion model 81A. Data such as the expansion model 81A may be stored in an external memory with which the terminal apparatus 80 can communicate instead of the memory 81 (or in addition to the memory 81).

The display 82 displays various types of information. For example, the display 82 displays medical images (CT images) expanded by the processing circuit, GUI images through which various operations from an operator are received, and the like. The display 82 is a liquid crystal display, a CRT, an organic EL display, or the like, for example.

The input interface 83 receives various input operations from an operator and outputs electrical signals representing details of the received input operations to the processing circuit 90. For example, the input interface 83 receives various settings and the like when an image is expanded. For example, the input interface 83 is realized by a mouse, a keyboard, a touch panel, a trackball, a switch, a button, a joystick, a camera, an infrared sensor, a microphone, or the like.

The network connection circuit 84 includes, for example, a network card having a printed circuit board, a wireless communication module, or the like. The network connection circuit 84 implements an information communication protocol in accordance with a form of a network to be connected thereto.

The processing circuit 90 is an example of the second processor. The processing circuit 90 executes, for example, an image expansion function 91, a display control function 92, and the like. These components are realized by a hardware processor executing a program (software) stored in the memory 81, for example. The hardware processor has been described above. The program may be directly incorporated into the circuit of the hardware processor instead of being stored in the memory 81. In this case, the hardware processor realizes functions by reading and executing the program incorporated into the circuit. The hardware processor is not limited to a configuration as a single circuit and may be configured as a single hardware processor by combining a plurality of independent circuits to realize respective functions. Furthermore, a plurality of components may be integrated into a single hardware processor to realize respective functions.

The image expansion function 91 acquires intermediate data from the database server 400 via the network NW using the network connection circuit 84 and inputs the intermediate data to the expansion model 81A to output medical image data for viewing which has a quantity greater than that of the intermediate data. The display control function 92 causes the display 82 to display an image based on the medical image data for viewing.

[With Respect to Various Models]

Figure 4:
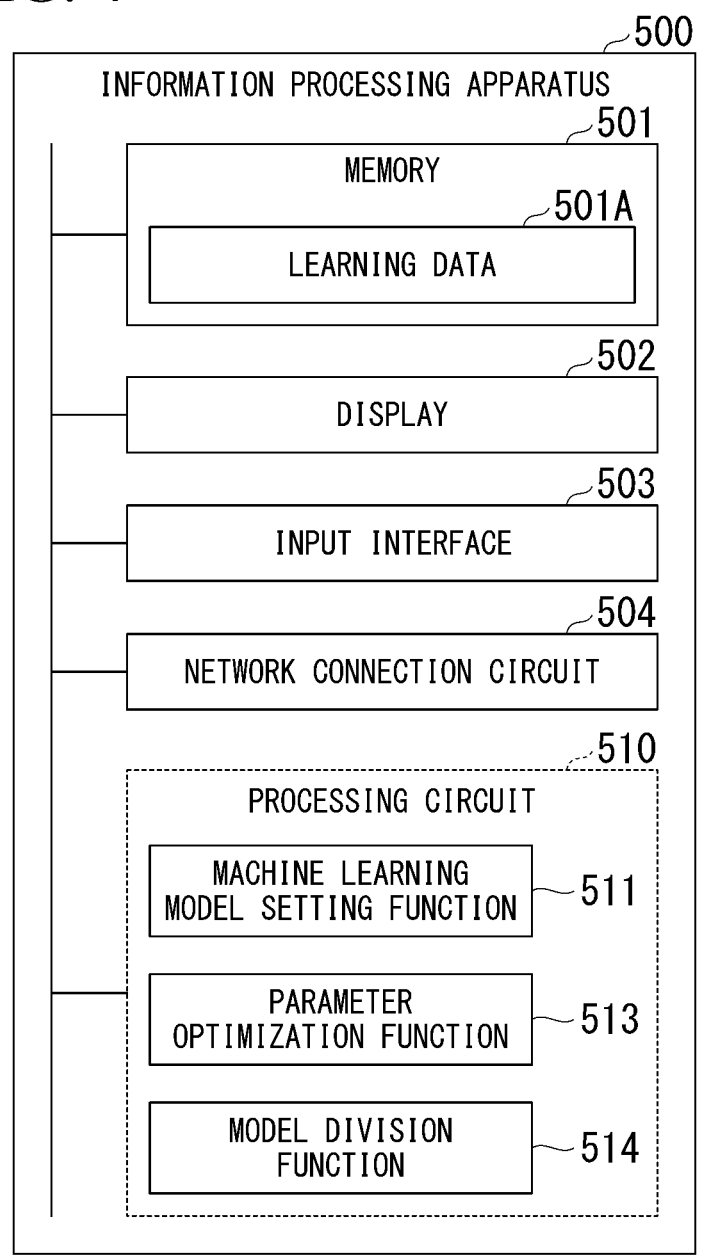
FIG. 4 is a configuration diagram of an information processing apparatus which generates a trained model.

Hereinafter, generation and use of the compression model 41A, the expansion model 81A, and the trained model that is a source of the compression model 41A and the expansion model 81A will be described. The trained model is generated by any information processing apparatus. FIG. 4 is a configuration diagram of an information processing apparatus 500 that generates the trained model. The information processing apparatus 500 includes, for example, a memory 501, a display 502, an input interface 503, a network connection circuit 504, and a processing circuit 510.

The memory 501 is realized by, for example, a semiconductor memory element such as a RAM or a flash memory, a hard disk, an optical disc, or the like. The memory 501 stores, for example, learning data 501A. Data such as the learning data 501A may be stored in an external memory with which the information processing apparatus 500 can communicate instead of the memory 501 (or in addition to the memory 501).

The display 502 displays various types of information. For example, the display 502 displays medical images for viewing expanded by the processing circuit, GUI images through which various operations from an operator are received, and the like. The display 502 is a liquid crystal display, a CRT, an organic EL display, or the like, for example.

The input interface 503 receives various input operations from an operator and outputs electrical signals representing details of the received input operations to the processing circuit 510. For example, the input interface 503 receives initial settings and the like of a machine learning model. For example, the input interface 503 is realized by a mouse, a keyboard, a touch panel, a trackball, a switch, a button, a joystick, a camera, an infrared sensor, a microphone, or the like.

The network connection circuit 504 includes, for example, a network card having a printed circuit board, a wireless communication module, or the like. The network connection circuit 504 implements an information communication protocol in accordance with a form of a network to be connected thereto.

The processing circuit 510 executes, for example, a machine learning model setting function 511, a parameter optimization function 513, a model division function 514, and the like. These components are realized by a hardware processor executing a program (software) stored in the memory 501, for example. The hardware processor has been described above. The program may be directly incorporated into the circuit of the hardware processor instead of being stored in the memory 501. In this case, the hardware processor realizes functions by reading and executing the program incorporated into the circuit. The hardware processor is not limited to a configuration as a single circuit and may be configured as a single hardware processor by combining a plurality of independent circuits to realize respective functions. Furthermore, a plurality of components may be integrated into a single hardware processor to realize respective functions. The processing circuit 510 is an example of a third processor.

Figure 5:
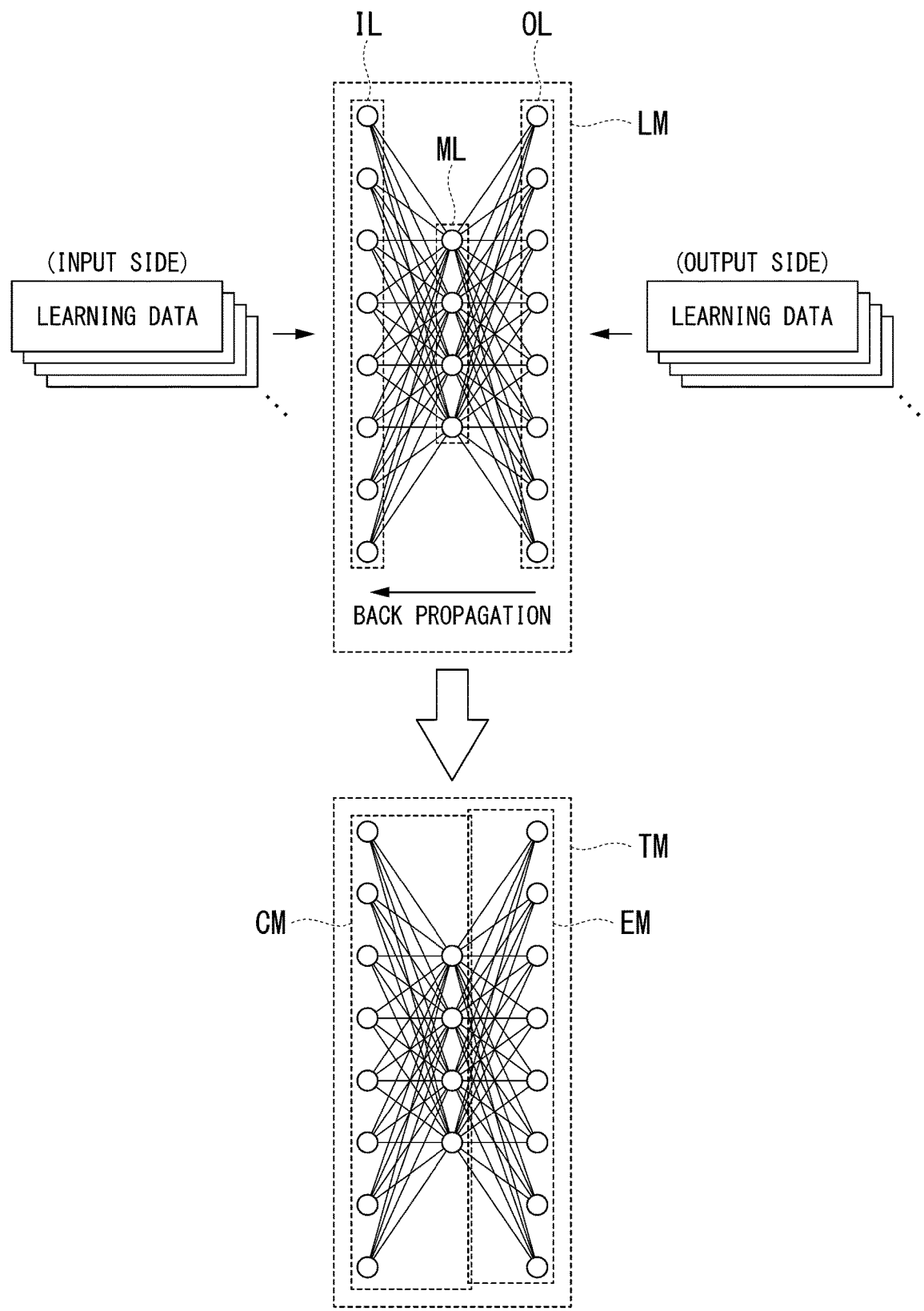
FIG. 5 is a diagram for describing functions of a processing circuit.

FIG. 5 is a diagram for describing functions of the processing circuit 510. The processing circuit 510 applies a plurality of sets of learning data of an input side and learning data (teacher data, correct answer data, and labels) of an output side to a machine learning model LM and adjusts parameters of the machine learning model LM using a method such as back propagation such that residuals between outputs of the machine learning model LM and the learning data of the output side decrease. The learning data of the input side is an example of first medical image data and the learning data of the output side is an example of second medical image data.

The machine learning model LM includes an input layer IL having a first number of nodes, an output layer OL having a second number of nodes, and a middle layer ML that is a layer between the input layer and the output layer and has a number of nodes less than any of the first number of node and the second number of nodes. A trained model TM also has the same structure. Although only the input layer IL, one middle layer, and the output layer OL are shown for simplification of illustration in FIG. 5, a plurality of middle layers may be present in practice. The illustrated numbers of nodes are less than actual numbers of nodes. The machine learning model LM is not limited to an all-coupling neural network and may have any coupling structure. The machine learning model is a deep neural network using a convolution neural network, for example.

The learning data of the input side is a plurality of pieces of medical image data stored in the memory 510 as the learning data 501A and is medical image data generated by the diagnostic apparatus 200 such as the X-ray CT apparatus 1. In the first embodiment, the learning data of the input side and the learning data of the output side which is the same as the learning data of the input side are used. Accordingly, the first number of nodes is the same as the second number of nodes in the first embodiment.

The machine learning model setting function 511 performs initial setting of the machine learning model LM on the basis of a setting operation performed on the input interface 503, or the like. The initial setting is, for example, to set the number of nodes and a coupling relationship of the neural network, the number of layers, and the like. Such initial setting may be automatically performed by the machine learning model setting function 511 on the basis of a requested compression ratio.

The parameter optimization function 513 adjusts parameters of the machine learning model LM by performing processing such as the aforementioned back propagation. When learning with respect to a predetermined number of sets of learning data is performed, a machine learning model LM at the final point in time becomes the trained model TM.

The model division function 514 divides the trained model TM to generate a compression model CM and an expansion model EM. The compression model CM outputs intermediate data with a quantity less than that of input medical image data (third medical image data) when the medical image data is input to the input layer IL having first number of nodes. A middle layer that outputs the intermediate data, that is, a middle layer that is the boundary between the compression model CM and the expansion model EM, may be a layer having a smallest number of nodes in the trained model TM or a layer deviating to the side of the input layer or the output layer compared to the layer having the smallest number of nodes. In the example of FIG. 5, the middle layer that outputs the intermediate data is a layer deviating to the side of the output layer compared to the layer having the smallest number of nodes.

Figure 6:
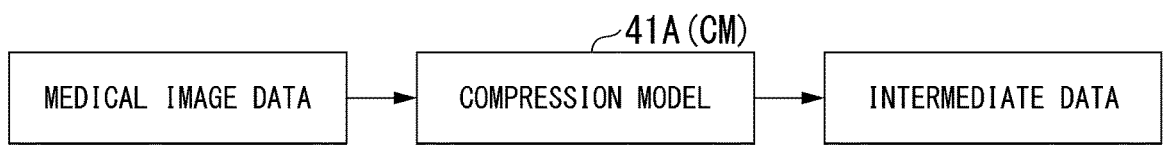
FIG. 6 is a diagram briefly showing a functions of an image compression function.

The compression model CM generated by the information processing apparatus 500 is stored in the memory 41 of the X-ray CT apparatus 1 as the compression model 41A. The image compression function 57 generates intermediate data by inputting medical image data generated by the X-ray CT apparatus 1 to the compression model 41A and transmits the intermediate data to the database server 400. FIG. 6 is a diagram briefly showing the function of the image compression function 57.

Figure 7:
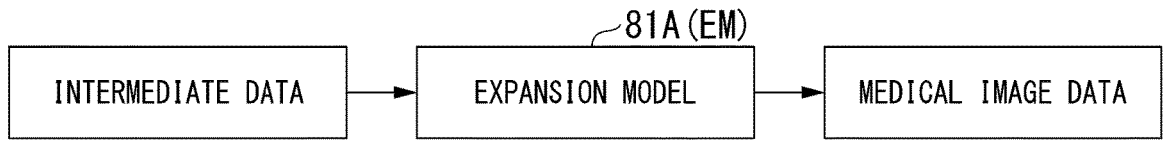
FIG. 7 is a diagram briefly showing a function of an image expansion function.

The expansion model EM generated by the information processing apparatus 500 is stored in the memory 81 of the terminal apparatus 80 as the expansion model 81A. The image expansion function 91 acquires intermediate data from the database server 400 via the network NW using the network connection circuit 84 and inputs the intermediate data to the expansion model 81A to output medical image data (fourth medical image data) with a quantity greater than that of the intermediate data. FIG. 7 is a diagram briefly showing the function of the image expansion function 91. The medical image data expanded in this manner has been trained such that it becomes approximate to the medical image data generated in the X-ray CT apparatus 1 and thus has visibility close thereto. As a result, the medial information processing system can maintain a desired level of definition after expansion. In addition, the compression model CM outputs intermediate data with a quantity less than that of input medical image data within a range in which the definition after expansion can be maintained. As a result, the medical information processing system can reduce resource consumption with respect to communication and data storage.

Although the middle layers in the machine learning model and the trained model have a smaller number of nodes than those of the input layers and the output layers in the above description, the middle layers may be set such that the number of bits (number of digits) retained by nodes becomes less than those of the input layers and the output layers instead thereof (or in addition thereto). The same applies to a second embodiment and the following.

Figure 8:
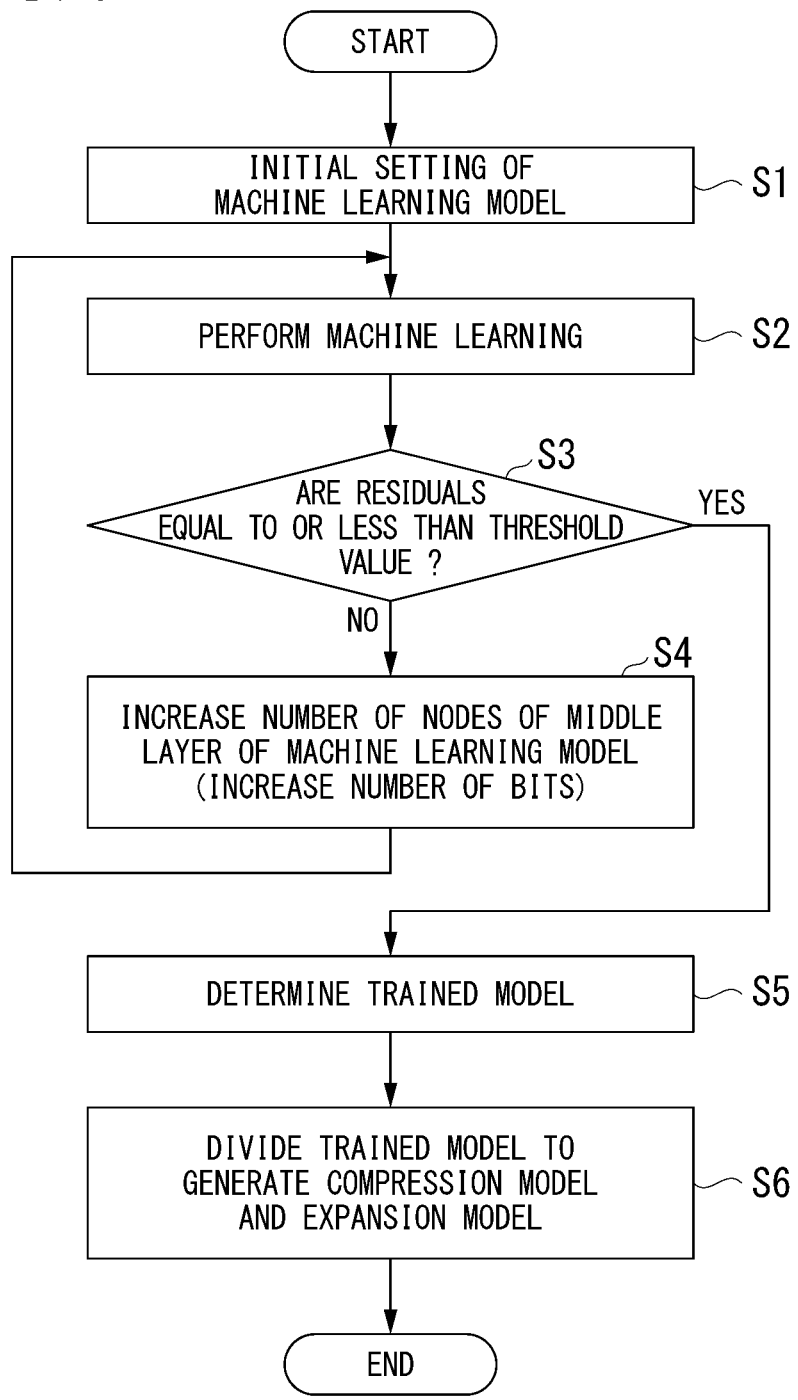
FIG. 8 is a flowchart showing an example of a processing flow executed by the processing circuit.

The machine learning model setting function 511 may dynamically perform resetting of a machine learning model on the basis of learning results instead of performing setting of the machine learning model in a fixed manner. FIG. 8 is a flowchart showing an example of a processing flow executed by the processing circuit 510.

First, the machine learning model setting function 511 performs initial setting of a machine learning model (step S1). The initial setting is performed such that the number of nodes of a middle layer sufficiently decreases and thus a requested compression ratio is satisfied.

Subsequently, the parameter optimization function 513 performs machine learning (step S2). Then, the machine learning model setting function 511 determines whether residuals (e.g., sum of squares of errors for each element) between values of an output layer and learning data of an output side are equal to or less than a threshold value (step S3). When the residuals exceed the threshold value, the machine learning model setting function 511 increases the number of nodes of the middle layer of the machine learning model (and/or increases the number of bits retained by nodes of the middle layer) and resets a machine learning model (S4) and the parameter optimization function 513 re-performs machine learning (step S2).

When a result of execution of machine learning once or more as described above is that residuals become equal to or less than the threshold value, the parameter optimization function 513 determines a machine learning model at the final point in time as a trained model (step S5). Then, the model division function 514 divides the trained model to generate a compression model and an expansion model. According to such processing, it is possible to maintain a desired level of definition after expansion. Meanwhile, instead of processing shown in FIG. 8, processing may be performed in a direction in which the number of nodes or the number of bits gradually decreases or processing of finely adjusting the number of nodes or the number of bits such that it increases or decreases may be performed as long as residuals are equal to or less than the threshold value.

According to the medical information processing system of the above-described first embodiment, it is possible to reduce resource consumption while maintaining a desired level of definition after expansion because compression and expansion are performed using a compression model including an input layer and a middle layer and an expansion model including an output layer from two trained models obtained by dividing a trained model integrally trained on the basis of the middle layer, respectively.

Second Embodiment

Figure 9:
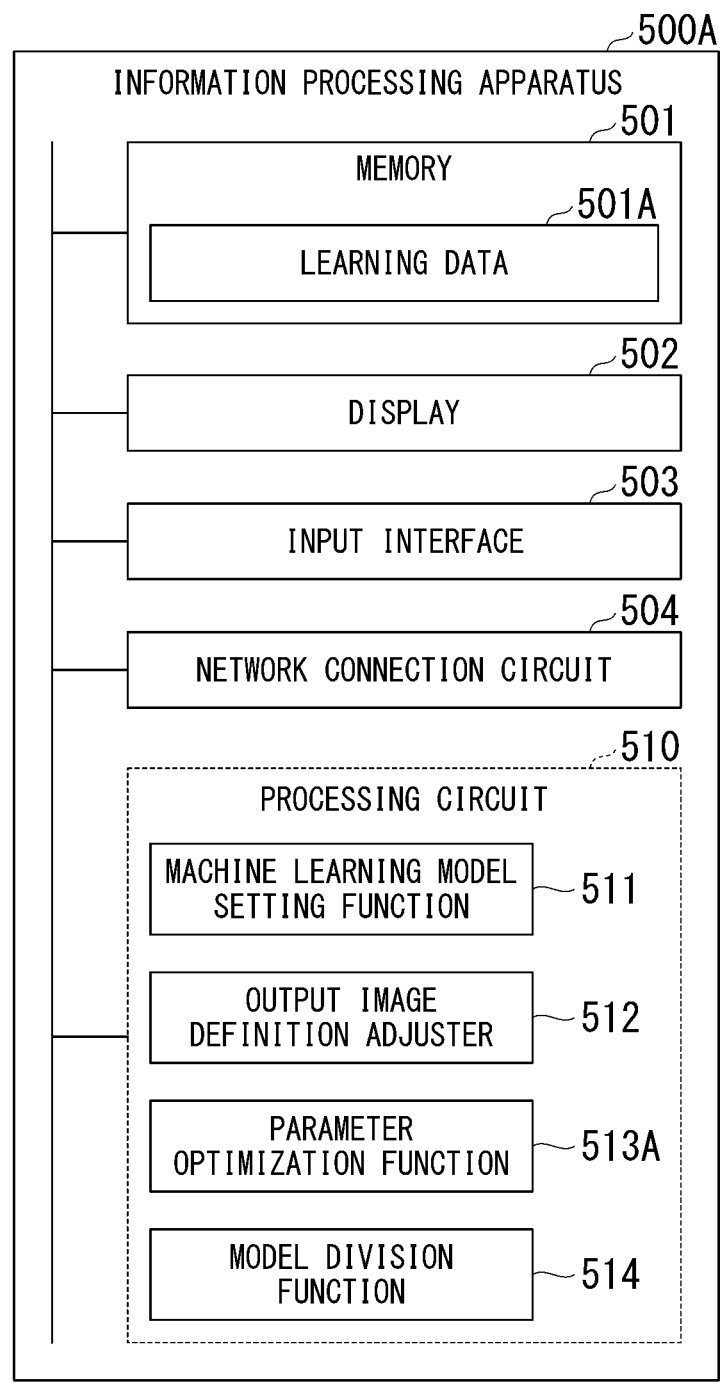
FIG. 9 is a configuration diagram of an information processing apparatus according to a second embodiment.

Hereinafter, a second embodiment will be described. The second embodiment differs from the first embodiment with respect to a trained model generation procedure. Accordingly, description will focus on such differences. FIG. 9 is a configuration diagram of an information processing apparatus 500A according to the second embodiment. The information processing apparatus 500A further includes an output image definition adjuster 512 as compared to the information processing apparatus 500 of the first embodiment. In addition, the parameter optimization function differs from that of the first embodiment and thus it is represented by 513A.

In the second embodiment, learning data of an input side is given attributes such as parts to be diagnosed (e.g., a head, a liver, a lung field, a heart, and the like) and/or an object of diagnosis. The output image definition adjuster 512 adjusts the definition of learning data of an output side in response to the attributes. For example, the output image definition adjuster 512 adjusts the definition of learning data of the output side such that the definition increases in the case of parts of which detailed structures need to be viewed, such as coronary arteries and a lung field and decreases in the case of parts having low frequency forms when the structures thereof are imaged, such as a liver and the heart muscle. When learning data with high definition is prepared, the output image definition adjuster 512 uses learning data of the input side as learning data of the output side as it is or uses image data obtained by performing noise reduction processing on the learning data of the input side as learning data of the output side. On the other hand, when learning data of the output side with low definition is prepared, the output image definition adjuster 512 uses image data obtained by performing fast Fourier transform (FFT) processing on learning data of the input side as learning data of the output side or uses image data obtained by performing low pass filtering on learning data of the input side as learning data of the output side. Accordingly, a trained model for high definition and a trained model for low definition are generated. Although it is assumed that two types of learning data of learning data with high definition and learning data with low definition are prepared by the output image definition adjuster 512 in the following description, learning data may be classified into three types or more according to definition. Learning data with high definition is an example of second medical image data and learning data with low definition is an example of fifth medical image data. Meanwhile, although there are cases in which people perceive an image in low resolution in which noise has been reduced as an image with high visibility, it is assumed that "definition is high" means "resolution is high" in the present description.

The parameter optimization function 513A according to the second embodiment performs machine learning such that parts corresponding to compression models in a trained model for high definition and a trained model for low definition are identical to each other. Specifically, the parameter optimization function 513A generates a trained model for high definition first, fixes a part corresponding to a compression model and then performs machine learning to generate a trained model for low definition. This order may be reversed.

Figure 10:
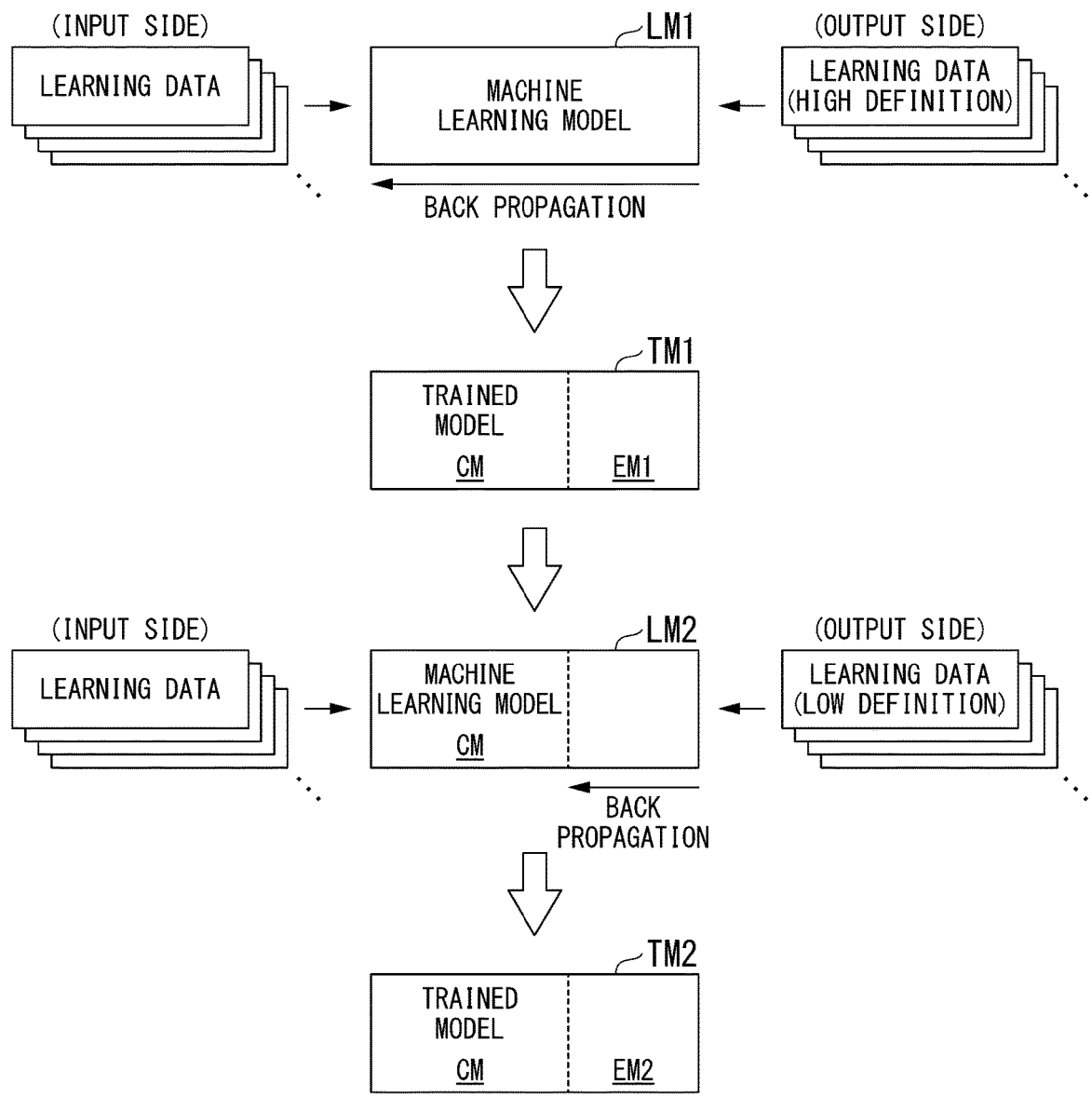
FIG. 10 is a diagram for describing a function of a parameter optimization function.

FIG. 10 is a diagram for describing the function of the parameter optimization function 513A. First, the parameter optimization function 513A performs machine learning of a first step using learning data of an input side and learning data of an output side as in the first embodiment. Here, the learning data of the output side is learning data with higher definition than that of learning data used for machine learning of a second step. For example, in machine learning of the first step, the learning data of the input side and the learning data of the output side, which are identical to each other, are used. The parameter optimization function 513 adjusts parameters of the machine learning model LM by performing processing such as the aforementioned back propagation. When learning with respect to a predetermined number of sets of learning data is performed, a machine learning model LM1 at the final point in time becomes a trained model TM1. The trained model TM1 is divided into a compression model CM and an expansion model EM1.

Subsequently, the parameter optimization function 513A performs machine learning of the second step using the same learning data of the input side as that in the machine learning of the first step as learning data of the input side and using learning data with lower definition that in the machine learning of the first step. Here, the parameter optimization function 513A uses a machine learning model LM2 that has taken over the part of the compression model CM in the trained model TM1, fixes the part of the compression model CM (without propagating error) and performs machine learning. The number of nodes of the input layer of the part of the compression model CM in the machine learning model LM2 is the same as the number of nodes of the input layer of the machine learning model LM1 in the first step. The number of nodes (an example of a third number of nodes) of the output layer of the part of an expansion model EM2 in the machine learning model LM2 may be the same as or different from (less than) the number of nodes of the output layer of the machine learning model LM1 in the first step. When learning with respect to a predetermined number of sets of learning data is performed, the machine learning model LM2 at the final point in time becomes a trained model TM2. The expansion model EM2 is cut out from the trained model TM2 because the compression model CM does not change from that in the first step.

The compression model CM generated by the information processing apparatus 500A is stored in the memory 41 of the X-ray CT apparatus 1 as the compression model 41A. The expansion models EM1 and EM2 generated by the information processing apparatus 500A are stored in the memory 81 of the terminal apparatus 80 as two types of expansion models 81A. The two types of expansion models 81A are a model that expands an image with high definition and a model that expands an image with low definition. A user of the terminal apparatus 80 can cause the display 82 to display medical image with desired definition by properly using models depending on purposes.

According to the above-described second embodiment, it is possible to reduce resource consumption while maintaining a desired level of definition after expansion as in the first embodiment. In addition, according to the second embodiment, it is possible to display medical images with a desired definition by preparing two or more types of expansion models having different definitions after expansion.

Third Embodiment

Hereinafter, a third embodiment will be described. In the third embodiment, learning data of an output side is acquired by performing processing on a part of learning data of an input side. More specifically, when the learning data of the input side includes a plurality of parts including a first part and a second part, the learning data of the output side is acquired by performing processing of making definition different in the first part and the second part on the learning data of the input side. Performing processing of making definition different may mean that processing such as filter processing and FFT processing is performed on one side and is not performed on the other side or that processing such as filter processing and FFT processing is performed on both sides to different degrees of processing or in different types of processing.

Figure 11:
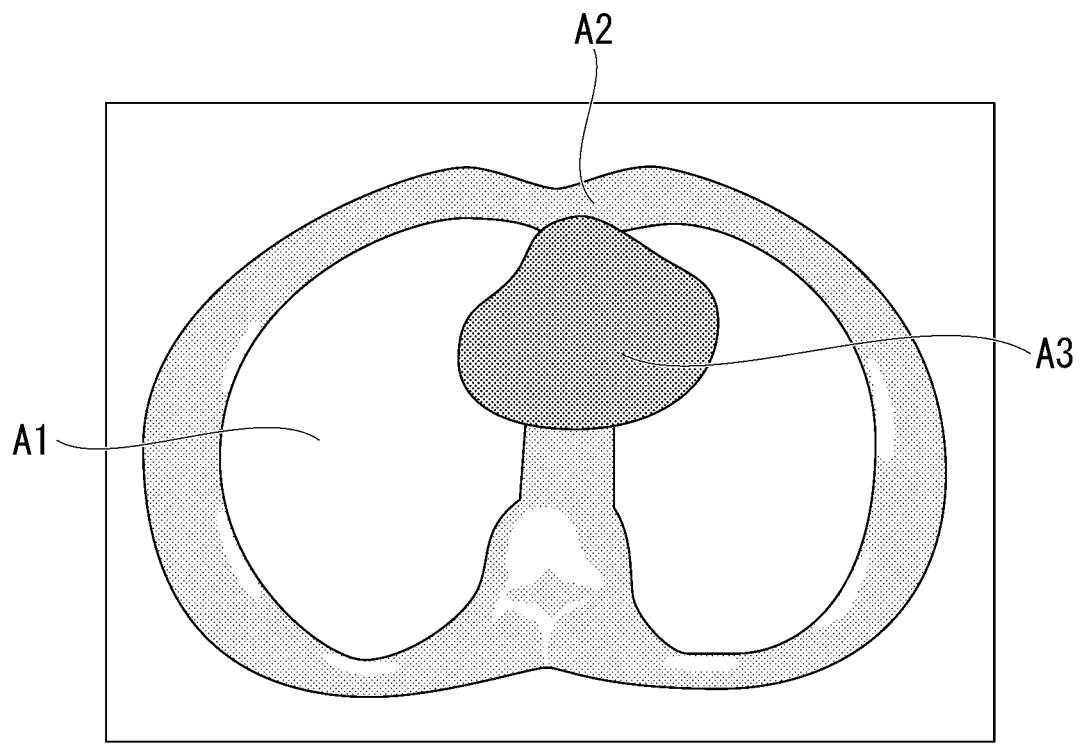
FIG. 11 is a diagram for describing processing of an output image definition adjuster.

Hereinafter, an information processing apparatus according to the third embodiment will be referred to as an information processing apparatus 500B and an output image definition adjuster according to the third embodiment will be referred to as an output image definition adjuster 512B although configurations thereof will not be illustrated. The output image definition adjuster 512B performs or does not perform processing on learning data of an input side for each part. FIG. 11 is a diagram for describing processing of the output image definition adjuster 512B. This figure shows an example in which learning data is an axial section with respect to chest examination. A lung field is reflected in an area A1 in this learning data. Since the lung field has a high contrast and a fine structure, the output image definition adjuster 512B maintains a high definition with respect to the area A1. Coronary arteries are reflected in an area A2. Since it is desirable to view a detained shape of the coronary arteries, the output image definition adjuster 512B maintains a high definition with respect to the area A2. The heart muscle is reflected in an area A3. Since the heart muscle has a relatively uniform structure, the output image definition adjuster 512B decreases the definition with respect to the area A3.

Upon execution of such processing, it is suitable to assign a label representing a part to each pixel or a pixel group in the learning data. A label is assigned using a technique of automatically identifying a part by extracting anatomical feature points from an image. Then, the output image definition adjuster 512B can automatically carrying on processing without receiving designation of a part from a user. The present invention is not limited thereto and the information processing apparatus 500B may receive designation of a part through the input interface 503.

Meanwhile, when an area corresponding to the coronary arteries is set, for example, it is suitable to perform area expansion from an area represented by a label or an area designated by a user with respect to a specific part such as the coronary arteries because it is desirable to increase the definition including edges and calcification.

When the learning data of the output side is set in this manner, it is conceived that the definition decreases in both intermediate data and an image after expansion. Consequently, it is possible to increases a compression degree with respect to a part that need not be observed in detail and thus can effectively reduce resource consumption. Furthermore, since it is possible to decrease a compression degree with respect to a part that needs to be observed in detail, it is possible to maintain a desired level of definition after expansion.

According to the above-described third embodiment, it is possible to effectively reduce resource consumption while maintaining a desired level of definition after expansion.

Although change of trained models during operation (when the X-ray CT apparatus compresses medical image data or the terminal apparatus expands medical image data) is not mentioned in each of the above-described embodiments, it is possible to perform adjustment such as decreasing the number of bits of the compression model or the expansion model even during operations of the apparatuses as well as during learning if differences between a reconstructed image and an expanded image are small, for example.

According to at least one embodiment described above, it is possible to reduce resource consumption while maintaining a desired level of definition after expansion by including the first processor (e.g., the processing circuit 50) configured to output intermediate data with a quantity less than that of the third medical image data by inputting the third medical image data to a compression model including an input layer and a middle layer from two trained models obtained by dividing, on the basis of the middle layer, a trained model which includes the input layer having the first number of nodes, an output layer having the second number of nodes, and the middle layer that is interposed between the input layer and the output layer and has a number of nodes less than the first number of nodes and the second number of nodes, and has been trained such that the second medical image data is output from the output layer by inputting the first medical image data to the input layer, and the second processor (e.g., the processing circuit 90) configured to output the fourth medical image data with a quantity greater than that of the intermediate data by inputting the intermediate data acquired from the first processor via the network to an expansion model including the output layer from the two trained models.

While preferred embodiments of the invention have been described and illustrated above, it should be understood that these are exemplary of the invention and are not to be considered as limiting. Additions, omissions, substitutions, and other modifications can be made without departing from the spirit or scope of the present invention. Accordingly, the invention is not to be considered as being limited by the foregoing description, and is only limited by the scope of the appended claims.

What is claimed is:

1. A medical information processing system comprising:
a first processing circuitry; and
a second processing circuitry,
the first processing circuitry being configured to output intermediate data with a quantity less than that of third medical image data by inputting the third medical image data to a compression model including an input layer and a middle layer from two trained models obtained by dividing, on the basis of the middle layer, a trained model which includes the input layer having a first number of nodes, an output layer having a second number of nodes, and the middle layer that is interposed between the input layer and the output layer and has a number of nodes less than the first number of nodes and the second number of nodes, and has been trained such that second medical image data is output from the output layer by inputting first medical image data to the input layer,
the second processing circuitry being configured to output fourth medical image data with a quantity greater than that of the intermediate data by inputting the intermediate data acquired from the first processing circuitry via a network to an expansion model including the output layer from the two trained models,
wherein the second medical image data is obtained by performing processing on at least a part of the first medical image data, and
wherein the first medical image data is image data corresponding to an area including a first part and a second part, each of the first part and the second part is automatically identified by extracting anatomical feature points from the first medical image data, and the second medical image data is obtained by performing processing of making a definition different in the first part and the second part on the first medical image data.

2. The medical information processing system according to claim 1, further comprising a third processing circuitry configured to generate the trained model on the basis of a machine learning model,
wherein, when a result of execution of machine learning on the machine learning model is that residuals between values of an output layer and learning data of an output side exceed a threshold value, the third processing circuitry increases a number of nodes of a middle layer of the machine learning model, increases a number of bits retained by the nodes of the middle layer, resets the machine learning model, and re-executes machine learning.

3. The medical information processing system according to claim 1, further comprising a third processing circuitry configured to generate the trained model on the basis of a machine learning model,
wherein, when a result of execution of machine learning on the machine learning model is that residuals between values of an output layer and learning data of an output side exceed a threshold value, the third processing circuitry increases a number of nodes of a middle layer of the machine learning model, resets the machine learning model, and re-executes machine learning.

4. The medical information processing system according to claim 1, further comprising a third processing circuitry configured to generate the trained model on the basis of a machine learning model,
wherein, when a result of execution of machine learning on the machine learning model is that residuals between values of an output layer and learning data of an output side exceed a threshold value, the third processing circuitry increases a number of bits retained by the nodes of the middle layer, resets the machine learning model, and re-executes machine learning.

5. The medical information processing system according to claim 1, further comprising a third processing circuitry configured to generate the trained model on the basis of a machine learning model,
wherein, when a result of execution of machine learning on the machine learning model is that residuals between values of an output layer and learning data of an output side are equal to or less than a threshold value, the third processing circuitry decreases a number of nodes of a middle layer of the machine learning model, decreases a number of bits retained by the nodes of the middle layer, resets the machine learning model, and re-executes machine learning.

6. The medical information processing system according to claim 1, further comprising a third processing circuitry configured to generate the trained model on the basis of a machine learning model,
wherein, when a result of execution of machine learning on the machine learning model is that residuals between values of an output layer and learning data of an output side are equal to or less than a threshold value, the third processing circuitry decreases a number of nodes of a middle layer of the machine learning model, resets the machine learning model, and re-executes machine learning.

7. The medical information processing system according to claim 1, further comprising a third processing circuitry configured to generate the trained model on the basis of a machine learning model,
wherein, when a result of execution of machine learning on the machine learning model is that residuals between values of an output layer and learning data of an output side are equal to or less than a threshold value, the third processing circuitry decreases a number of bits retained by the nodes of the middle layer, resets the machine learning model, and re-executes machine learning.

8. The medical information processing system according to claim 1,
wherein the second processing circuitry outputs sixth medical image data which has a quantity greater than that of the intermediate data and is different from the fourth medical image data by inputting the intermediate data to a second expansion model including a second output layer from two trained models obtained by dividing, on the basis of a second middle layer, a second trained model which includes a second input layer having the first number of nodes, the second output layer having a third number of nodes, and the second middle layer that is interposed between the second input layer and the second output layer and has a number of nodes less than the first number of nodes and the third number of nodes, and has been trained such that fifth medical image data different from the second medical image data is output from the second output layer by inputting the first medical image data to the second input layer.

9. The medical information processing system according to claim 8,
wherein the second trained model is a model trained in a state in which a part corresponding to the compression model included in the trained model is fixed.

10. A medical information processing apparatus comprising a first processing circuitry configured to output intermediate data with a quantity less than that of third medical image data by inputting the third medical image data to a compression model including an input layer and a middle layer from two trained models obtained by dividing, on the basis of the middle layer, a trained model which includes the input layer having a first number of nodes, an output layer having a second number of nodes, and the middle layer that is interposed between the input layer and the output layer and has a number of nodes less than the first number of nodes and the second number of nodes, and has been trained such that second medical image data is output from the output layer by inputting first medical image data to the input layer,
wherein the second medical image data is obtained by performing processing on at least a part of the first medical image data, and
wherein the first medical image data is image data corresponding to an area including a first part and a second part, each of the first part and the second part is automatically identified by extracting anatomical feature points from the first medical image data, and the second medical image data is obtained by performing processing of making a definition different in the first part and the second part on the first medical image data.

11. A medical information processing apparatus comprising a second processing circuitry configured to output fourth medical image data with a quantity greater than that of intermediate data by inputting the intermediate data output from a compression model including an input layer and a middle layer to an expansion model including an output layer from two trained models obtained by dividing, on the basis of the middle layer, a trained model which includes the input layer having a first number of nodes, the output layer having a second number of nodes, and the middle layer that is interposed between the input layer and the output layer and has a number of nodes less than the first number of nodes and the second number of nodes, and has been trained such that second medical image data is output from the output layer by inputting first medical image data to the input layer,
wherein the second medical image data is obtained by performing processing on at least a part of the first medical image data, and
wherein the first medical image data is image data corresponding to an area including a first part and a second part, each of the first part and the second part is automatically identified by extracting anatomical feature points from the first medical image data, and the second medical image data is obtained by performing processing of making a definition different in the first part and the second part on the first medical image data.

* * * * *